US012667499B2

(12) United States Patent
Weber et al.

(10) Patent No.: US 12,667,499 B2
(45) Date of Patent: Jun. 30, 2026

(54) ABSORBENT ARTICLE WITH IMPROVED CHANNELED CORE AND METHOD OF MAKING

(71) Applicants: ONTEX BV, Buggenhout (BE); ONTEX GROUP NV, Erembodegem (BE)

(72) Inventors: Ainas Weber, Bad Neuenahr-Ahrweiler (DE); Alissa Idelson, Rheinbach (DE)

(73) Assignees: Ontex BV, Buggenhout (BE); Ontex Group NV, Erembodegem (BE)

( * ) Notice: Subject to any disclaimer, the term of this patent is extended or adjusted under 35 U.S.C. 154(b) by 632 days.

(21) Appl. No.: 18/008,729

(22) PCT Filed: Jun. 1, 2021

(86) PCT No.: PCT/EP2021/064648
§ 371 (c)(1),
(2) Date: Dec. 7, 2022

(87) PCT Pub. No.: WO2021/249824
PCT Pub. Date: Dec. 16, 2021

(65) Prior Publication Data
US 2023/0210702 A1     Jul. 6, 2023

(30) Foreign Application Priority Data

Jun. 8, 2020    (EP) .................................... 20178776

(51) Int. Cl.
A61F 13/15          (2006.01)
A61F 13/536         (2006.01)
(Continued)

(52) U.S. Cl.
CPC .. A61F 13/15699 (2013.01); A61F 13/15707 (2013.01); A61F 13/536 (2013.01);
(Continued)

(58) Field of Classification Search
CPC .......... A61F 13/15699; A61F 13/15707; A61F 13/536; A61F 2013/15406;
(Continued)

(56) References Cited

U.S. PATENT DOCUMENTS

| | | | | |
|---|---|---|---|---|
| 2012/0312491 A1* | 12/2012 | Jackels | ............... | A61F 13/4704 |
| | | | | 162/297 |
| 2014/0163511 A1* | 6/2014 | Roe | ........................ | A61F 13/532 |
| | | | | 604/385.101 |
| 2015/0342796 A1* | 12/2015 | Bianchi | ............. | A61F 13/15634 |
| | | | | 604/378 |

FOREIGN PATENT DOCUMENTS

| | | | | |
|---|---|---|---|---|
| EP | 2886092 A1 * | 6/2015 | ....... | A61F 13/49001 |
| EP | 3342386 A1 | 7/2018 | | |

(Continued)

OTHER PUBLICATIONS

International Search Report and Written Opinion for PCT/EP2021/064648, mailed Sep. 10, 2021.

*Primary Examiner* — Jacqueline F Stephens
(74) *Attorney, Agent, or Firm* — VIVICAR Law, PLLC

(57) ABSTRACT

An absorbent article comprising: a liquid permeable top-sheet, a liquid impermeable backsheet, and an absorbent core positioned between said topsheet and backsheet, wherein the absorbent core comprises an absorbent material, said absorbent material comprising cellulose fibers and/or superabsorbent polymers, and wherein said absorbent material is contained within at least one core wrap substrate enclosing said absorbent material, and wherein a top layer of said core wrap is adhered to a bottom layer of said core wrap by a first adhesive to form one or more channel forming areas substantially free of said absorbent material, wherein said top layer comprises said first adhesive arranged to define a first adhesive area and said bottom layer comprises a second adhesive arranged to define a second area, wherein (Continued)

said first adhesive area is greater than said second adhesive area, and wherein said first and second adhesive areas comprise one or more adhesive stripes, wherein at least one of said adhesive stripes of the first adhesive area overlap said channel forming areas.

20 Claims, 8 Drawing Sheets

(51) Int. Cl.
　　　*A61F 13/534*　　　(2006.01)
　　　*A61F 13/539*　　　(2006.01)
(52) U.S. Cl.
　　　CPC ............... *A61F 2013/15406* (2013.01); *A61F 2013/1591* (2013.01); *A61F 2013/53445* (2013.01); *A61F 2013/5349* (2013.01); *A61F 2013/53908* (2013.01)

(58) Field of Classification Search
　　　CPC .... A61F 2013/1591; A61F 2013/53445; A61F 2013/5349
　　　See application file for complete search history.

(56) References Cited

FOREIGN PATENT DOCUMENTS

| | | |
|---|---|---|
| EP | 3453368 A1 | 3/2019 |
| EP | 3527183 A1 | 8/2019 |
| WO | 2012170778 A1 | 12/2012 |
| WO | 2012170779 A1 | 12/2012 |
| WO | 2012170781 A1 | 12/2012 |
| WO | 2012170808 A1 | 12/2012 |
| WO | 2018122117 A1 | 7/2018 |
| WO | 2018172860 A1 | 9/2018 |

* cited by examiner

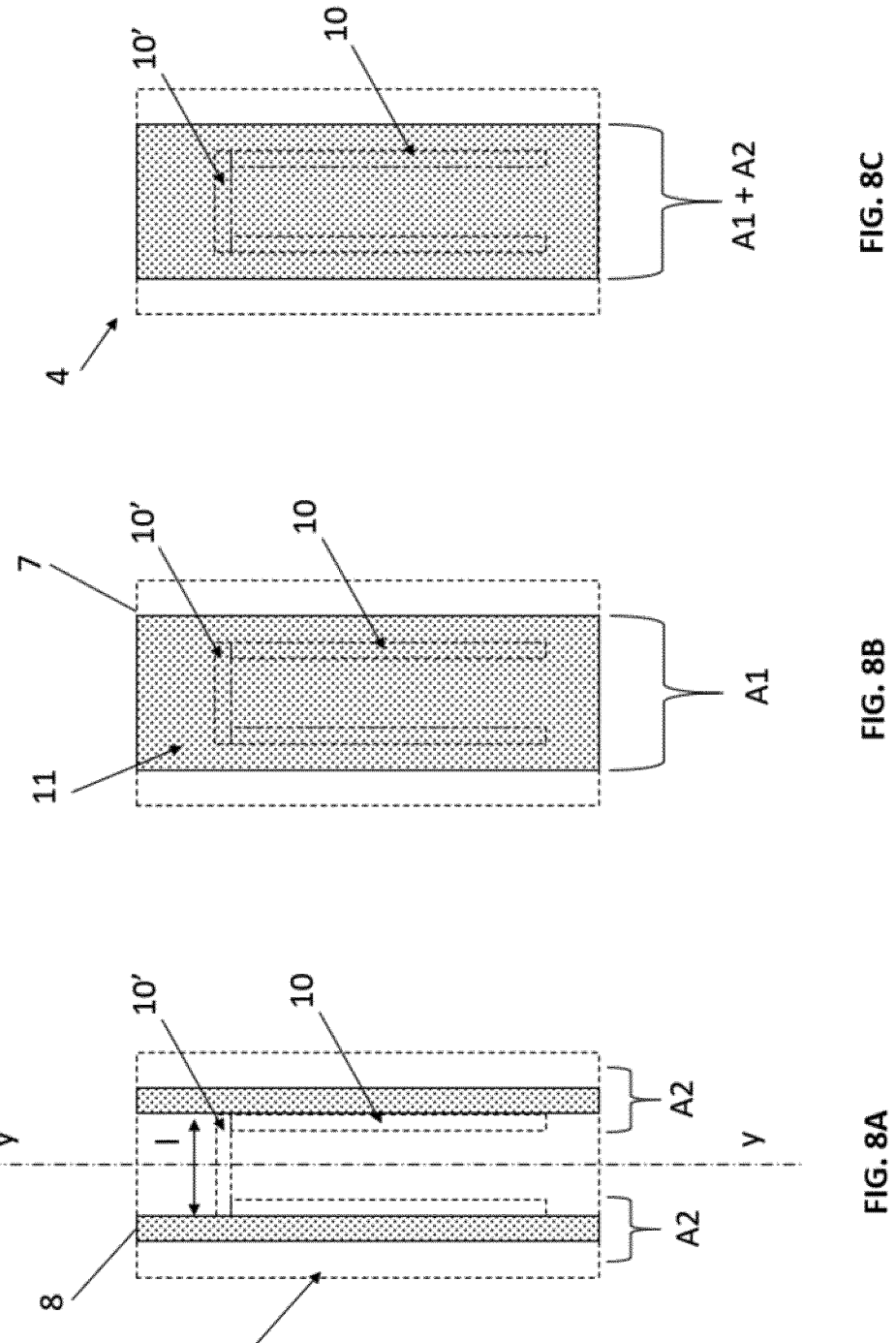

ABSORBENT ARTICLE WITH IMPROVED CHANNELED CORE AND METHOD OF MAKING

CROSS-REFERENCE TO RELATED APPLICATIONS

This application is the national stage application of corresponding international application number PCT/EP2021/064648, filed Jun. 1, 2021, which claims priority to and the benefit of European application no. 20178776.9, filed Jun. 8, 2020, which is hereby incorporated by reference in its entirety.

TECHNICAL FIELD

The disclosure relates to absorbent articles such as disposable absorbent articles, preferably selected from the group consisting of diapers (whether for baby or adults), pants (whether for baby or adults), pantiliners, briefs, sanitary napkins, and combinations thereof.

BACKGROUND

Absorbent articles comprising different channel structure designs for enhancing liquid distribution and maximising the use of the core have been developed.

WO2012/170778 (Rosati et al., see also WO2012/170779, WO2012/170781 and WO2012/1708008) discloses absorbent structures that comprise superabsorbent polymer, optionally a cellulosic material, and at least a pair of substantially longitudinally extending channels. The core wrap can be adhesively bonded through the channels to form a channel bond. The channel bonds may be permanent, so that their integrity is at least partially maintained both in dry and wet state. As the absorbent structure absorbs liquid and swells, the absorbent structure takes a three-dimensional shape with the channels becoming visible. The channels provide improved fit and/or liquid acquisition/transportation, and/or improved performance throughout the use of the absorbent structure.

Further improvements in channel geometries for better core utilisation and liquid distribution are described in EP3342386 describing an absorbent core comprising substantially continuous zones of one or more high fluid distribution structures and discontinuous zones of fluid absorption structures surrounding the one or more high fluid distribution structures, wherein the one or more high fluid distribution structures are arranged to distribute fluid across the absorbent core at a speed that is faster than the speed of fluid distribution across the absorbent core by said discontinuous fluid absorption structures, and wherein said continuous zones extend along a path that is substantially parallel to at least a portion of the perimeter of the core, said portion of the perimeter of the core comprising at least a portion of the sides of the core and one of the ends of the core.

Investment in improved processes for providing channelled absorbent articles has been made. For example WO2018/172860 describes a method for forming an absorbent pad comprising a first layer, a second layer and an absorbent material interposed between the first and the second layer and arranged according to a spreading pattern M1 having at least one channel which is free of absorbent material, comprises a step of feeding a first web (NW1), intended to form the first layer of the pad; a step of feeding a second web (NW2), intended to form the second layer of the pad; a step of spreading the absorbent material on the first web (NW1) according to the spreading pattern M1; a step of joining the first and second webs (NW1, NW2), a step of removing any absorbent material that may be present in the channel.

Another example is EP3453368 that describes a method for manufacturing an absorbent article, said method comprising: a. applying a first binder in a first area on a first side of first sheet material; b. applying a second binder in a second area on a first side of second sheet material; c. applying an absorbent material on the first side of the first sheet material; d. attaching the first sheet material to the second sheet material with the first sides facing each other, such that at least one attachment zone is formed; wherein one of the first sheet material and the second sheet material is a top core wrap sheet material and the other is a back core wrap sheet material; and the first area is arranged at a distance from the intended position of the at least one attachment zone, wherein the first area and the second area are substantially complementary after the step of attaching the wrap sheets to each other. This arrangement generally results in substantially the entire surface of the absorbent article provided with binder on either the first sheet material or the second sheet material. It has however been observed that this arrangement results in undesirable stiffening effects within the absorbent article due to the high surface area of coverage of the adhesive region formed as well as negative impacts on core stability, bonding strength and resilience in the channels, and liquid permeability through the core.

There is therefore still a need to provide improved absorbent articles comprising channel forming areas and methods of making. In particular there is a need for absorbent articles comprising channel forming areas and methods of making that allow for strong bonding strength and resilience in the channel forming areas whilst retaining optimal core stability and/or improving core flexibility and/or liquid intake permeability therethrough.

SUMMARY

In a first aspect, the disclosure relates to an absorbent article comprising: a liquid permeable topsheet, a liquid impermeable backsheet, and an absorbent core positioned between said topsheet and backsheet, wherein the absorbent core comprises an absorbent material, said absorbent material comprising cellulose fibers and/or superabsorbent polymers, and wherein said absorbent material is contained within at least one core wrap substrate enclosing said absorbent material, and wherein a top layer of said core wrap is adhered to a bottom layer of said core wrap by a first adhesive to form one or more channel forming areas substantially free of said absorbent material, (preferably wherein said channel forming areas have a length extending along a longitudinal axis and the absorbent core has a length extending along said longitudinal axis and wherein the length of said channel forming areas is from 10% to 95%, preferably from 12% to 90%, even more preferably from 14% to 85%, even more preferably from 15% to 80%, even more preferably from 18% to 75%, even more preferably from 20% to 70%, of the length of said absorbent core) typically being arranged such that said channel forming areas form one or more channels that are circumscribed by absorbent material (alternatively or in addition the channel forming areas are typically being formed inboard of a perimeter of the core such that said channel forming areas do not extend up to the edges of the core formed by the perimeter of said core and are typically separated therefrom by absorbent material), wherein said top layer comprises said first adhesive arranged to define a first adhesive area and said bottom layer comprises a second adhesive arranged to define a second area, wherein said first adhesive area is greater than said second adhesive area, and wherein said first and second adhesive areas comprise a plurality of adhesive stripes, wherein at least one, preferably at least two, of said adhesive stripes of the first adhesive area overlap said channel forming areas, and typically at least one of said adhesive stripes is positioned inboard and/or outboard of said channel forming areas such that it does not overlap said channel forming areas. Preferably wherein the first adhesive area is equal to the sum of all areas of said stripes of said first adhesive, and typically wherein the second adhesive area is equal to the sum of all areas of said stripes of said second adhesive.

In a second aspect, the disclosure relates to a method for making an absorbent article comprising one or more channel forming areas, the method comprising the steps of: i. providing a mold comprising a non-porous insert therein, wherein the mold is in fluid communication with an under-pressure source except for said insert; ii. providing a first nonwoven web; iii. applying a plurality of adhesive stripes to said first nonwoven web, said adhesive stripes comprising a second adhesive applied by a second adhesive applicator; iv. depositing said first nonwoven web to said mold such that said second adhesive faces away from said mold; v. depositing an absorbent material, comprising cellulose fibers and/or superabsorbent polymer particles, over at least a portion of a surface of said nonwoven web comprising said second adhesive; vi. removing said absorbent material from areas of the nonwoven web corresponding to said insert; vii. applying a plurality of adhesive stripes to a second nonwoven web, said adhesive stripes comprising a first adhesive applied by a first adhesive applicator; viii. depositing said second nonwoven web directly or indirectly over the absorbent material, such to sandwich said absorbent material between top and bottom core wrap layers formed by said first and second nonwoven webs; ix. joining said top and bottom core wrap layers together at least in the areas of the nonwoven webs corresponding to the insert to form an absorbent core having one or more channel forming areas substantially free of absorbent material; x. optionally joining an acquisition distribution system (herein also referred to as acquisition distribution layer) to said absorbent core, typically a skin facing surface of said upper core wrap layer; xi. optionally laminating said absorbent core and acquisition distribution system between a liquid pervious topsheet and a liquid impervious backsheet; wherein said first adhesive forms a first adhesive area and said second adhesive forms a second adhesive area, wherein said first adhesive area is greater than said second adhesive area, and wherein at least two of the stripes of said first adhesive area overlap said channel forming areas. Preferably wherein the first adhesive area is equal to the sum of all areas of said stripes of said first adhesive, and typically wherein the second adhesive area is equal to the sum of all areas of said stripes of said second adhesive.

In another aspect, the disclosure relates to an absorbent article comprising: a liquid permeable topsheet, a liquid impermeable backsheet, and an absorbent core positioned between said topsheet and backsheet, wherein the absorbent core comprises an absorbent material, said absorbent material comprising cellulose fibers and/or superabsorbent polymers, and wherein said absorbent material is contained within at least one core wrap substrate enclosing said absorbent material, and wherein a top layer of said core wrap is adhered to a bottom layer of said core wrap by a first adhesive to form one or more channel forming areas substantially free of said absorbent material, (preferably wherein said channel forming areas have a length extending along a longitudinal axis and the absorbent core has a length extending along said longitudinal axis and wherein the length of said channel forming areas is from 10% to 95%, preferably from 12% to 90%, even more preferably from 14% to 85%, even more preferably from 15% to 80%, even more preferably from 18% to 75%, even more preferably from 20% to 70%, of the length of said absorbent core,) typically being arranged such that said channel forming areas form one or more channels that are circumscribed by absorbent material, wherein said top layer comprises said first adhesive arranged to define a first adhesive area and said bottom layer comprises a second adhesive arranged to define a second area, wherein said first adhesive area is greater than said second adhesive area, and wherein said first and second adhesive areas comprise one or more, preferably a plurality, of adhesive stripes, wherein at least one of said adhesive stripes of the first adhesive area overlap said channel forming areas. Preferably wherein the first adhesive area is equal to the sum of all areas of said stripes of said first adhesive, and typically wherein the second adhesive area is equal to the sum of all areas of said stripes of said second adhesive. Preferably wherein the first adhesive area comprises a single stripe of first adhesive and the second adhesive area comprises a plurality of stripes of second adhesive, and typically wherein the stripe of first adhesive overlaps with one or more stripes of said second adhesive.

BRIEF DESCRIPTION OF THE FIGURES

FIG. 8A-C schematically illustrate adhesive patterns according to embodiments of the present disclosure.

DETAILED DESCRIPTION

Figure 1A:
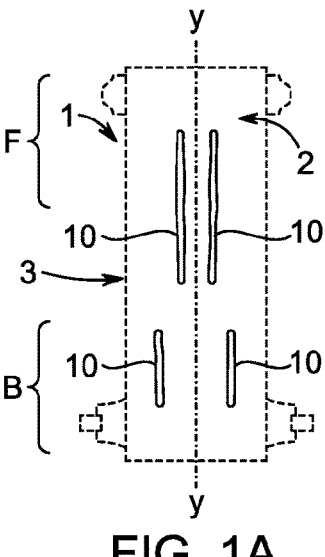
FIG. 1A-E Illustrates absorbent articles according to embodiments according to the present disclosure.
Figure 1B:
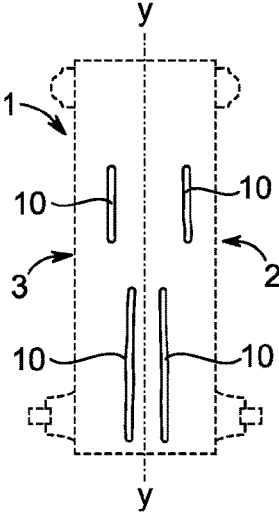
Figure 1C:
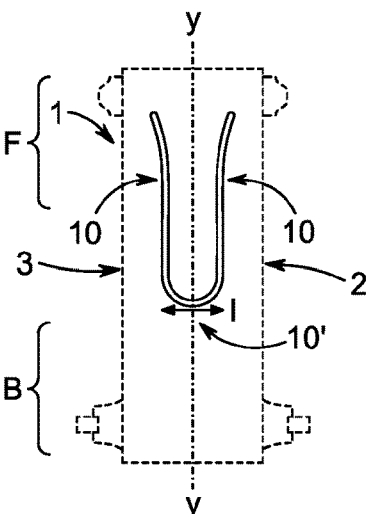
Figure 1D:
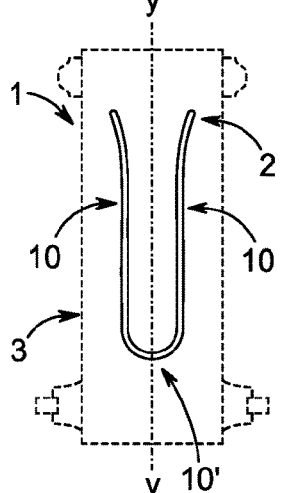
Figure 1E:
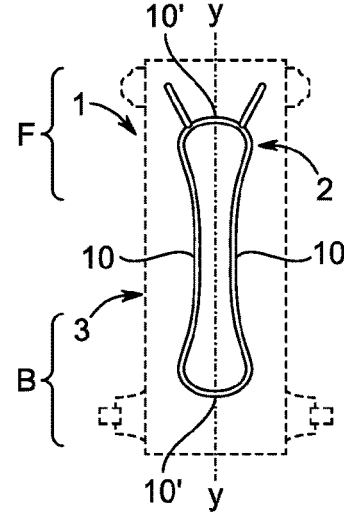

Unless otherwise defined, all terms used in disclosing characteristics of the disclosure, including technical and scientific terms, have the meaning as commonly understood by one of ordinary skill in the art to which this disclosure belongs. By means of further guidance, term definitions are included to better appreciate the teaching of the present disclosure.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +1-10% or less, more preferably +/−5% or less, even more preferably +1-1% or less, and still more preferably 4-0.1% or less of and from the specified value, in so far such variations are appropriate to perform in the disclosed disclosure. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The expression "% by weight" (weight percent), here and throughout the description unless otherwise defined, refers to the relative weight of the respective component based on the overall weight of the formulation.

The use of the term "layer" can refer, but is not limited, to any type of substrate, such as a woven web, nonwoven web, films, laminates, composites, elastomeric materials, or the like. A layer can be liquid and air permeable, permeable to air but impermeable to liquids, impermeable both to air and liquid, or the like. When used in the singular, it can have the dual meaning of a single element or a plurality of elements, such as a laminate.

"Laminate" refers to elements being attached together in a layered arrangement.

The term "spunbond fibers (or layer(s) or nonwovens)" refers to fibers formed by extruding molten thermoplastic polymers as filaments or fibers from a plurality of relatively fine, usually circular, capillaries of a spinneret, and then rapidly drawing the extruded filaments by an eductive or other well-known drawing mechanism to impart molecular orientation and physical strength to the filaments. The average diameter of spunbond fibers is typically in the range of from 15-60 µm or higher. The spinneret can either be a large spinneret having several thousand holes per meter of width or be banks of smaller spinnerets, for example, containing as few as 40 holes.

The term "spunbond meltblown spunbond" (SMS) nonwoven fabric as used herein refers to a multi-layer composite sheet comprising a web of meltblown fibers sandwiched between and bonded to two spunbond layers. A SMS nonwoven fabric can be formed in-line by sequentially depositing a first layer of spunbond fibers, a layer of meltblown fibers, and a second layer of spunbond fibers on a moving porous collecting surface. The assembled layers can be bonded by passing them through a nip formed between two rolls that can be heated or unheated and smooth or patterned. Alternately, the individual spunbond and meltblown layers can be pre-formed and optionally bonded and collected individually such as by winding the fabrics on wind-up rolls. The individual layers can be assembled by layering at a later time and bonded together to form a SMS nonwoven fabric. Additional spunbond and/or meltblown layers can be incorporated to form laminate layers, for example spunbond-meltblown-meltblown-spunbond (SMMS), or spunbond-meltblown (SM) etc. The recitation of numerical ranges by endpoints includes all numbers and fractions subsumed within that range, as well as the recited endpoints unless otherwise stated.

"Carded web (or layer(s) or nonwoven)" refers to webs that are made from staple fibers that are sent through a combing or carding unit, which opens and aligns the staple fibers in the machine direction to form a generally machine direction-oriented fibrous nonwoven web. The web is then bonded by one or more of several known bonding methods. Bonding of nonwoven webs may be achieved by a number of methods; powder bonding, wherein a powdered adhesive or a binder is distributed through the web and then activated, usually by heating the web and adhesive with hot air; pattern bonding, wherein heated calendar rolls or ultrasonic bonding equipment are used to bond the fibers together, usually in a localized bond pattern, though the web can be bonded across its entire surface if so desired; through-air bonding, wherein air which is sufficiently hot to soften at least one component of the web is directed through the web; chemical bonding using, for example, latex adhesives that are deposited onto the web by, for example, spraying; and consolidation by mechanical methods such as needling and hydroentanglement. Carded thermobonded nonwoven thus refers to a carded nonwoven wherein the bonding is achieved by use of heat.

The term "top sheet" refers to a liquid permeable material sheet forming the inner cover of the absorbent article and which in use is placed in direct contact with the skin of the wearer. The top sheet is typically employed to help isolate the wearer's skin from liquids held in the absorbent structure. The top sheet can comprise a nonwoven material, e.g. spunbond, meltblown, carded, hydroentangled, wetlaid etc. Suitable nonwoven materials can be composed of man-made fibres, such as polyester, polyethylene, polypropylene, viscose, rayon etc. or natural fibers, such as wood pulp or cotton fibres, or from a mixture of natural and man-made fibres. The top sheet material may further be composed of two fibres, which may be bonded to each other in a bonding pattern. Further examples of top sheet materials are porous foams, apertured plastic films, laminates of nonwoven materials and apertured plastic films etc. The materials suited as top sheet materials should be soft and non-irritating to the skin and be readily penetrated by body fluid, e.g. urine or menstrual fluid. The inner coversheet may further be different in different parts of the absorbent article. The top sheet fabrics may be composed of a substantially hydrophobic material, and the hydrophobic material may optionally be treated with a surfactant or otherwise processed to impart a desired level of wettability and hydrophilicity.

"Adhesive" typically means a formulation that generally comprises several components. These components typically include one or more polymers to provide cohesive strength (e.g., aliphatic polyolefins such as poly (ethylene-co-propylene) copolymer; ethylene vinyl acetate copolymers; styrene-butadiene or styrene-isoprene block copolymers; etc.); a resin or analogous material (sometimes called a tackifier) to provide adhesive strength (e.g., hydrocarbons distilled from petroleum distillates; rosins and/or rosin esters; terpenes derived, for example, from wood or citrus, etc.); perhaps waxes, plasticizers or other materials to modify viscosity (i.e., flowability) (examples of such materials include, but are not limited to, mineral oil, polybutene, paraffin oils, ester oils, and the like); and/or other additives including, but not limited to, antioxidants or other stabilizers. A typical hot-melt adhesive formulation might contain from about 15 to about 35 weight percent cohesive strength polymer or polymers; from about 50 to about 65 weight percent resin or other tackifier or tackifiers; from more than zero to about 30 weight percent plasticizer or other viscosity modifier; and optionally less than about 1 weight percent stabilizer or other additive. It should be understood that other adhesive formulations comprising different weight percentages of these components are possible.

The term "back sheet" refers to a material forming the outer cover of the absorbent article. The back sheet prevents the exudates contained in the absorbent structure from wetting articles such as bedsheets and overgarments which contact the disposable absorbent article. The back sheet may be a unitary layer of material or may be a composite layer composed of multiple components assembled side-by-side or laminated. The back sheet may be the same or different in different parts of the absorbent article. At least in the area of the absorbent medium the back sheet comprises a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The back sheet material may be breathable so as to allow vapour to escape from the absorbent material, while still preventing liquids from passing there through. Examples of breathable back sheet materials are porous polymeric films, nonwoven laminates of spunbond and meltblown layers and laminates of porous polymeric films and nonwoven materials.

"Acquisition and distribution layer", "ADL" or "surge management portion" refers to a sub-layer which preferably is a nonwoven wicking layer under the top sheet of an absorbent product, which speeds up the transport and improves distribution of fluids throughout the absorbent core. The surge management portion is typically less hydrophilic than the retention portion, and has the ability to quickly collect and temporarily hold liquid surges, and to transport the liquid from its initial entrance point to other parts of the absorbent structure, particularly the retention portion. This configuration can help prevent the liquid from pooling and collecting on the portion of the absorbent garment positioned against the wearer's skin, thereby reducing the feeling of wetness by the wearer. Preferably, the surge management portion is positioned between the top sheet and the retention portion.

As used herein, the term "transverse" or "lateral" refers to a line, axis, or direction which lies within the plane of the absorbent article and is generally perpendicular to the longitudinal direction.

"Dry-state" refers to the condition in which an absorbent article has not yet been saturated with exudates and/or liquid.

"Wet-state" refers to the condition in which an absorbent article has been saturated with exudates and/or liquid. Typically wherein at least 30 ml, preferably at least 40 ml, even more preferably at least 50 ml, most preferably from 60 ml to 800 ml, of exudate and/or liquid are contained in the absorbent article.

As used herein, the term "cellulosic" or "cellulose" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

"Superabsorbent polymer particles" or "SAPs" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In absorbent articles, such as diapers, incontinent diapers, etc., the particle size is typically ranging between 100 to 800 μm, preferably between 300 to 600 μm, more preferably between 400 to 500 μm. Superabsorbent materials suitable for use in the present disclosure are known to those skilled in the art, and may be in any operative form, such as particulate form, fibers and mixtures thereof. Generally stated, the "superabsorbent material" can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. The superabsorbent material may suitably be included in an appointed storage or retention portion of the absorbent system, and may optionally be employed in other components or portions of the absorbent article. The superabsorbent material may be included in the absorbent layer or other fluid storage layer of the absorbent article of the present disclosure in an amount up to about 90% by weight. Typically, the superabsorbent material, when present, will be included in an amount of about 20% to about 70% by weight, based on the total weight of the absorbent layer.

By "substantially", it is meant at least the majority of the structure referred to.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

The term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

"Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. Further, the elements can be joined directly together, or may have one or more elements interposed between them, all of which are connected together.

As used herein, the "body-facing" or "bodyside" or "skin-facing" surface means that surface of the article or component which is intended to be disposed toward or placed adjacent to the body (e.g. the face) of the wearer during ordinary use, while the "outward", "outward-facing" surface is on the opposite side, and is intended to be disposed to face away from the wearer's body during ordinary use.

Embodiments of the articles and processes according to the disclosure will now be described. It is understood that technical features described in one or more embodiments maybe combined with one or more other embodiments without departing from the intention of the disclosure and without generalization therefrom.

The Absorbent Article

Referring to FIGS. 1 to 5 and 7 to 8, the disclosure relates to an absorbent article (1) comprising: a liquid permeable topsheet (2), a liquid impermeable backsheet (3), and an absorbent core (4) positioned between said topsheet (2) and backsheet (3), wherein the absorbent core (4) comprises an absorbent material (5), said absorbent material comprising cellulose fibers and/or superabsorbent polymers, and wherein said absorbent material is contained within at least one core wrap substrate (6) enclosing said absorbent material, and wherein a top layer (7) of said core wrap is adhered to a bottom layer (8) of said core wrap by a first adhesive (11) to form one or more channel forming areas (10) substantially free of said absorbent material, the channel forming areas (10) typically being formed inboard of a perimeter of the core (4) such that said channel forming areas (10) do not extend up to the edges of the core formed by the perimeter of said core (4) but are typically separated therefrom by absorbent material, wherein said top layer (7) comprises said first adhesive (11) arranged to define a first adhesive area (A1) and said bottom layer (8) comprises a second adhesive (12) arranged to define a second area (A2), wherein said first adhesive area (A1) is greater than said second adhesive area (A2), and wherein said first and second adhesive areas (A1, A2) comprise one or more adhesive stripes, wherein at least one, preferably at least two, of said adhesive stripes of the first adhesive area (A1) overlap said channel forming areas (10), and typically at least one of said adhesive stripes is positioned inboard and/or outboard of said channel forming areas such that it does not overlap said channel forming areas. Preferably wherein the first adhesive area is equal to the sum of all areas of said stripes of said first adhesive, and typically wherein the second adhesive area is equal to the sum of all areas of said stripes of said second adhesive. Surprisingly, it has been found that by ensuring a different surface area of adhesive is used in top and bottom core wrap layers, and in particular that the adhesive surface area on the top core wrap layer is greater than that of the bottom core wrap layer allows for a significant improvement in flexibility of the core is achieved. This is achieved without compromise to the strength of the attachment in the channel forming areas. Moreover, without wishing to be bound by theory, applying more adhesive on the top layer compared to the bottom layer has the advantage that surface dryness of the absorbent system is likely to improve, for a solid adhesive connection between the upper core wrap and the surface of the absorbent core aids to prevent droplets of fluid remaining unabsorbed by the core, and thus surprisingly improving rewet performance.

In an embodiment, as exemplified in FIG. 7, the first adhesive area (A1) comprises one central stripe and at least two lateral stripes positioned outboard of said central stripe, wherein the central stripe is wider than said outer stripes and wherein said central stripe is sized to overlap at least a substantial portion, typically at least 80% of the total area, of the channel forming areas (10) and typically at least the transverse channel forming area(s) (10') (as generally described herein below). More preferably the central stripe has a width that is greater or equal to the sum of the widths of the channel forming area(s) (10) taken along a transverse axis being perpendicular to the longitudinal axis (y). Advantageously this arrangement allows for improved wet integrity of the channel forming area especially when transverse channel forming area(s) are used.

In an embodiment, as exemplified in FIG. 8, the first adhesive area (A1) comprises a single stripe of first adhesive having a width that is less than a width of the said top layer (7) of the core wrap (taken along a transverse axis being substantially perpendicular to the longitudinal axis y) and generally positioned centrally over the said top layer (7) and sized such to overlap a substantial portion, typically at least 80%, preferably at least 90%, more preferably 100%, of the channel forming areas (including, when present, the transverse channel forming area(s) (10'), as generally described herein below). This embodiment may be combined with any of the embodiments that follow, most preferably with embodiments that describe absorbent cores wherein, when seen from a planar view, the stripes of the first and second adhesive areas (A1, A1) overlap and form at least one, preferably a plurality, of stripes free of adhesive.

Typically, the channel forming areas described herein form one or more channels within the absorbent core that are visible in dry and/or wet state.

Figures 2A, 2B:
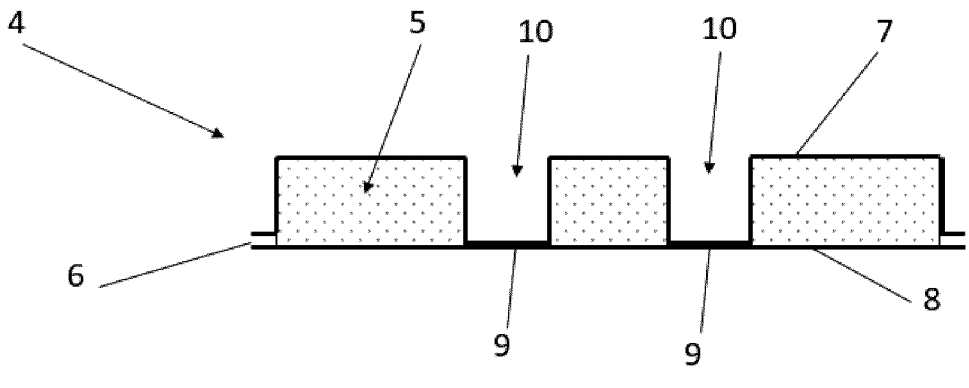
FIG. 2A-B schematically illustrate a cross-section of absorbent cores used in absorbent articles according to embodiments of the present disclosure.
Figures 3A, 3B, 3C:
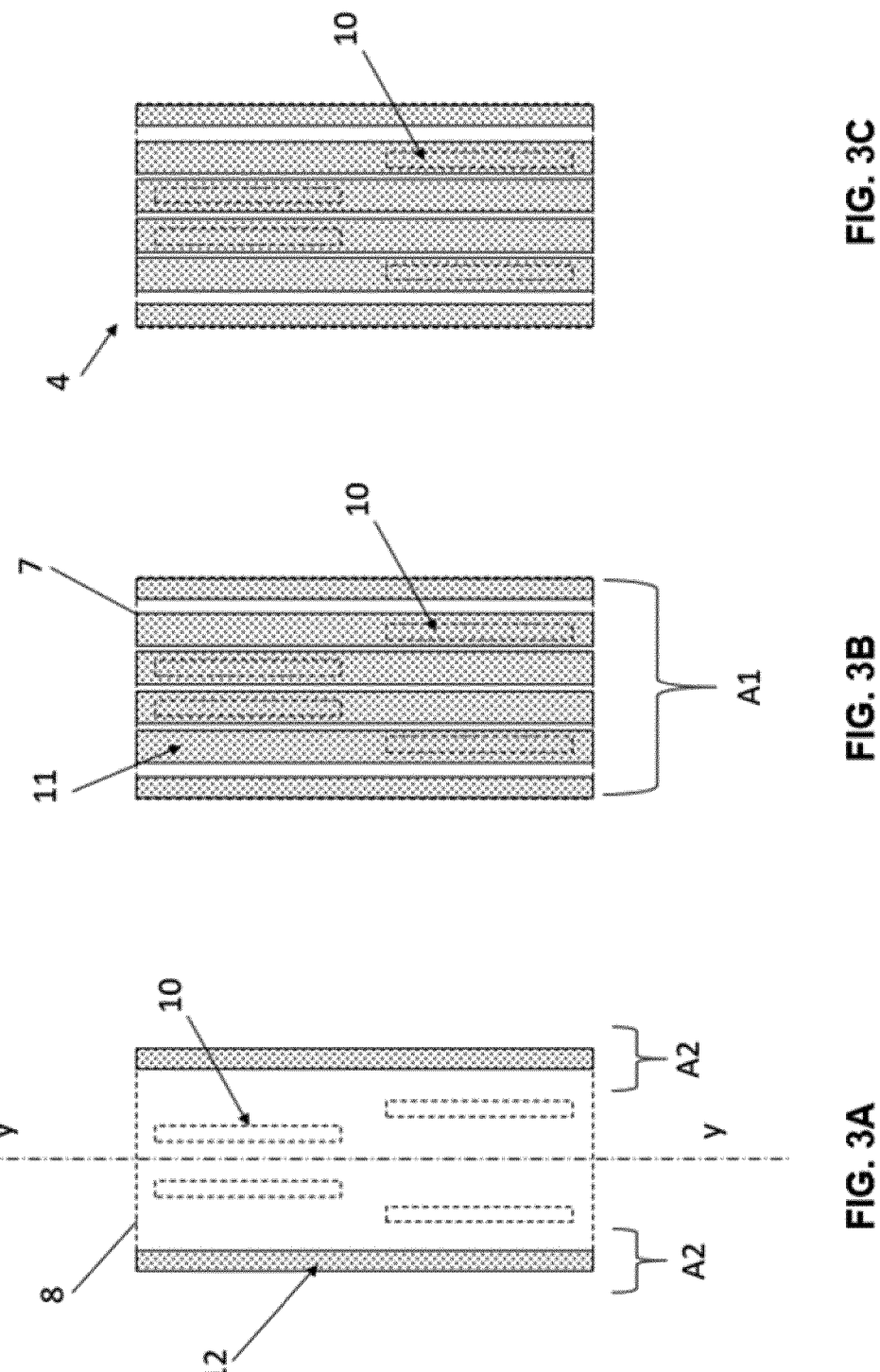
FIG. 3A-C schematically illustrate adhesive patterns according to embodiments of the present disclosure.
Figures 4A, 4B, 4C:
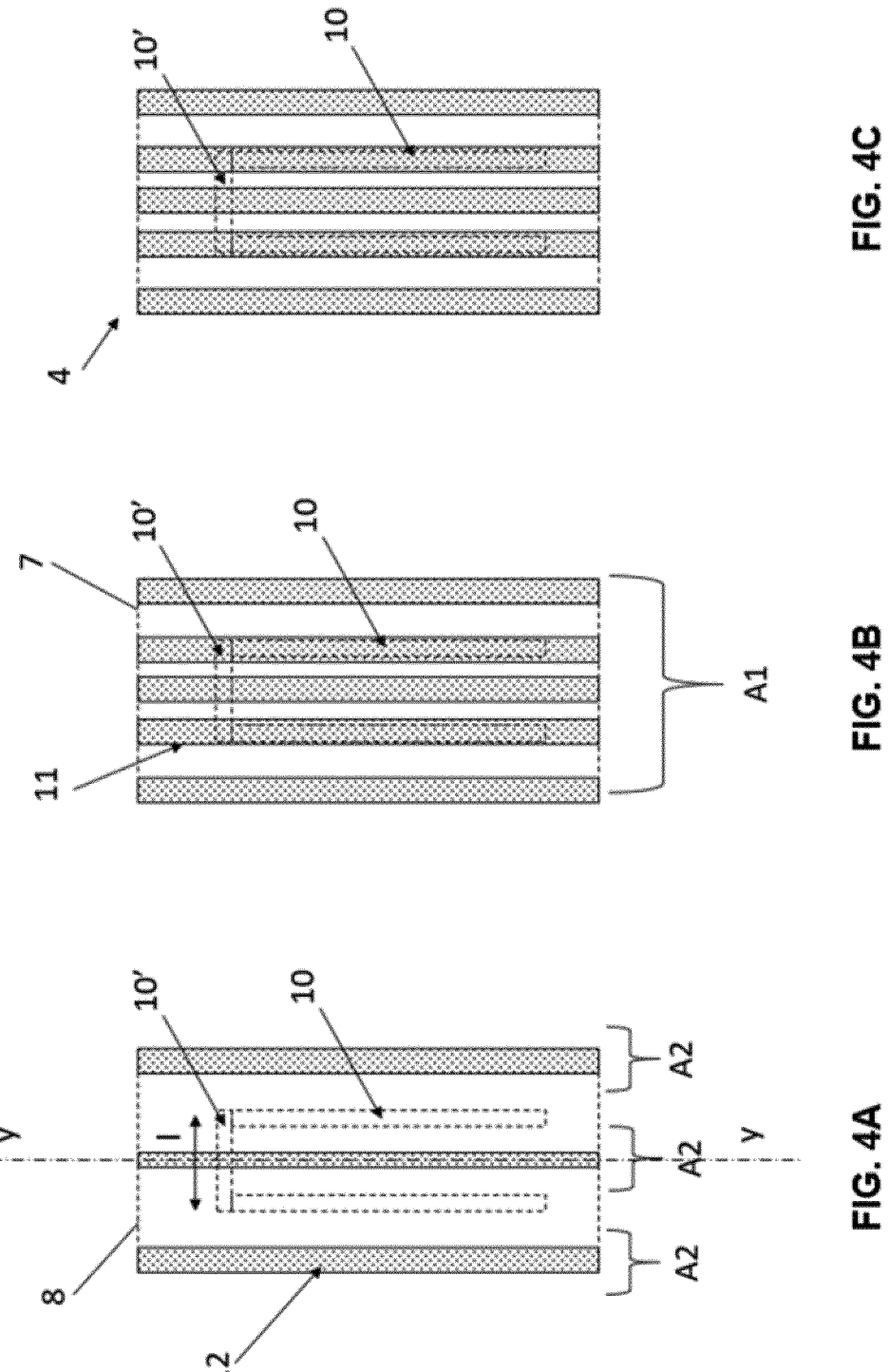
FIG. 4A-C schematically illustrate adhesive patterns according to embodiments of the present disclosure.

With particular reference to FIG. 2A-B, the channel forming areas (10) may be formed by joining the top and bottom layers (7,8) to each other at a bonding position (9) that can be a bottom position, middle position or upper position within the absorbent core cross-section, so long that a channel forming area(s) substantially free of absorbent material results therefrom.

Preferably, the first adhesive area (A1) and second adhesive area (A2) form an area ratio A1/A2 that is greater than 1.5, preferably the area ratio A1/A2 is from 2 to 15, preferably from 2.5 to 12, more preferably from 3 to 11.5. Surprisingly, these ranges are found to be most optimal for attaining the above mentioned advantages.

Preferably, the adhesive stripes referred to herein have the longest dimension that runs substantially parallel to the longitudinal axis (y). This arrangement allows to use an apparatus that applies continuous striped of adhesive along a machine direction (MD) and as such allowing much faster production speeds to be attained vs for example intermittent adhesive application.

In an embodiment, the channel forming areas have a length extending along a longitudinal axis and the absorbent core has a length extending along said longitudinal axis and wherein the length of said channel forming areas is from 10% to 95%, preferably from 12% to 90%, even more preferably from 14% to 85%, even more preferably from 15% to 80%, even more preferably from 18% to 75%, even more preferably from 20% to 70%, of the length of said absorbent core, typically such that at least one of, preferably each, said channel forming areas are circumscribed by absorbent material. Advantageously this helps against leakage a the perimeter of the core.

In a preferred embodiment, the second adhesive area (A2) consists of at least two spaced apart stripes of adhesive positioned outboard and/or inboard of the channel forming areas (10). Typically said stripes being spaced apart in a planar view (i.e. when looked at from a plane formed by the longitudinal axis y and a transverse axis perpendicular thereto as illustrated for example in FIGS. 3-5 and 7 to 8. Advantageously this allows to provide some core stability by partly immobilizing the absorbent material especially against lateral movement.

In a preferred embodiment, the first adhesive area (A1) consists of one or more spaced apart adhesive stripes wherein at least one, preferably at least two, more preferably at least three, even more preferably from 4 to 7, of said adhesive stripes is positioned outboard and/or inboard of the channel forming areas (10). Typically said stripes being spaced apart in a planar view (i.e. when looked at from a plane formed by the longitudinal axis y and a transverse axis perpendicular thereto as illustrated for example in FIGS. 3-5 and 7 to 8. Advantageously this allows to provide added core stability by partly immobilizing the absorbent material especially against lateral movement in regions inboard and/or outboard of the channel forming areas.

In a preferred embodiment, the at least two adhesive stripes of the first adhesive area (A1) that overlap said channel forming areas (10) comprise a first basis weight of said first adhesive, and wherein all other stripes of the first and second adhesive areas (A1, A2) comprise a second basis weight of first and/or second adhesive respectively, and wherein the first basis weight is from 150% to 800%, preferably from 200% to 750%, even more preferably from 250% to 600%, most preferably from 300% to 550%, greater than said second basis weight. Preferably, the first basis weight is from 2 g/m$^2$ to 8 g/m$^2$, preferably from 3 g/m$^2$ to 7 g/m$^2$, even more preferably from 3.5 g/m$^2$ to 6 g/m$^2$. Advantageously, this allows for improved bonding strength in the channel forming areas whilst reducing the amount of typically hydrophobic material in other areas of the core.

Preferably, the first and second adhesive areas (A1,A2) substantially overlap each other such that they are not complementary (typically when looked at in a planar view). This has the advantage of concentrating adhesive in parallel areas that permit for adhesive free areas in between with added flexibility enhancement, particularly lateral flexibility along the longitudinal axis y.

In an embodiment, the first adhesive area (A1) is arranged such that no adhesive is present between consecutive adhesive stripes, and wherein at least 2, preferably at least 3, more preferably from 4 to 10, of said stripes free of adhesive are comprised in the top layer (7) of the core wrap. Advantageously, this arrangement not only improves core flexibility as mentioned above, but further allows to delocalize hydrophobic effects that may be generated by the adhesive and thus permit good fluid handling properties of the core structure.

In an embodiment, the second area (A2) is arranged such that no adhesive is present between consecutive adhesive stripes, and wherein at least 1, preferably from 1 to 3, of said stripes free of adhesive are comprised in the bottom layer (8) of the core wrap, and preferably wherein at least 50%, preferably from 55% to 80%, of the surface area of said bottom layer (8) is free of adhesive. Advantageously this arrangement allows to significantly increase the flexibility of the resulting core.

In a highly preferred embodiment, the channel forming areas (10) comprise at least two longitudinal channel forming areas extending along said longitudinal axis (y) and oppositely disposed such that said longitudinal axis (y) extends therebetween, and at least one transverse channel forming area (10') extending substantially perpendicular to said longitudinal axis (y), preferably wherein said transverse channel forming area (10') connects to said longitudinal channel forming areas at a position being selected from the group consisting of the front (F) of said article, the back (B) of said article, and combinations thereof. This arrangement not only improves the fluid handling properties of the core across its width, in addition to its length, but further improve core flexing whilst still providing resistance to excessive sagging that would otherwise particularly be observed upon swelling of the absorbent material (in wet state) if only longitudinal channels are formed.

Preferably, at least one of the stripes, preferably only one of the stripes, of the first adhesive area (A1) overlap at least a portion of the transverse channel forming area (10'), and typically wherein none of the stripes of the second adhesive area (A2) overlap the transverse channel forming area (10').

In an embodiment, at least one of the stripes, preferably only one of the stripes, of the second adhesive area (A2) overlap at least a portion of the transverse channel forming area (10'). In this embodiment, said stripe typically substantially corresponds to the longitudinal centerline of the absorbent core. Preferably the stripe(s) of the second adhesive area (A2) overlapping at least a portion of the transverse channel forming area (10') has a smaller width than the stripe(s) of the first adhesive area (A1) overlapping at least a portion of the transverse channel forming area (10'), said width taken along a transversal axis of the absorbent core being substantially perpendicular to the longitudinal axis (y). Typically said overlapping stripe(s) (i.e. the referenced stripes of respective adhesive areas overlapping the transverse channel forming area) of said first and second adhesive areas (A1, A2) overlap each other when the top and bottom layers (7, 8) are joined. Advantageously this arrangement allows to minimize absorbent material contamination within the transverse channel forming area whilst retaining good cup shape formation in the longitudinal direction of the core for better fit in the crotch region of the wearer.

In a highly preferred embodiment, as exemplified in FIGS. 3C, 4C, 5C, 7C, and 8C, the adhesive stripes of the first and second adhesives (11,12) are arranged such that, when looked from a planar view, the absorbent core (4) comprises a plurality of stripes free of adhesive between top layer (7) and bottom layer (8), wherein said plurality of stripes free of adhesive material are positioned inboard and/or outboard of the channel forming areas (10, 10'). Advantageously this arrangement not only improves the effects of lateral flexibility of the core but further enhances liquid absorption therethrough.

In an embodiment, the channel forming areas (10) comprise at least one transverse channel forming area (10') having a length (1) extending along an axis perpendicular to the longitudinal axis (y), and wherein at least one of the stripes of adhesive of the first adhesive area (A1) and/or second adhesive area (A2) crosses said transverse channel forming area (10'), such that the transverse channel forming area (10') comprises said first adhesive (11) over a length that is from 0.251 to 1.001, preferably from 0.261 to 0.951, preferably from 0.31 to 0.91, even more preferably from 0.351 to 0.851, and/or wherein said transverse channel forming area (10') comprises said second adhesive (12) over a length that is less than 0.751, preferably less than 0.71, even more preferably from 01 to 0.651, even more preferably from 0.11 to 0.61, even more preferably from 0.151 to less than 0.51. Advantageously, this arrangement allows for formation of small areas adjacent the adhesive that are substantially free of absorbent material yet un-joined such to allow increased space for the neighbouring absorbent material to fill upon swelling thereof as liquid is absorbed. This is particularly beneficial for increasing flexibility in the lateral direction when the absorbent article is soiled (i.e. in wet state).

Figure 5C:
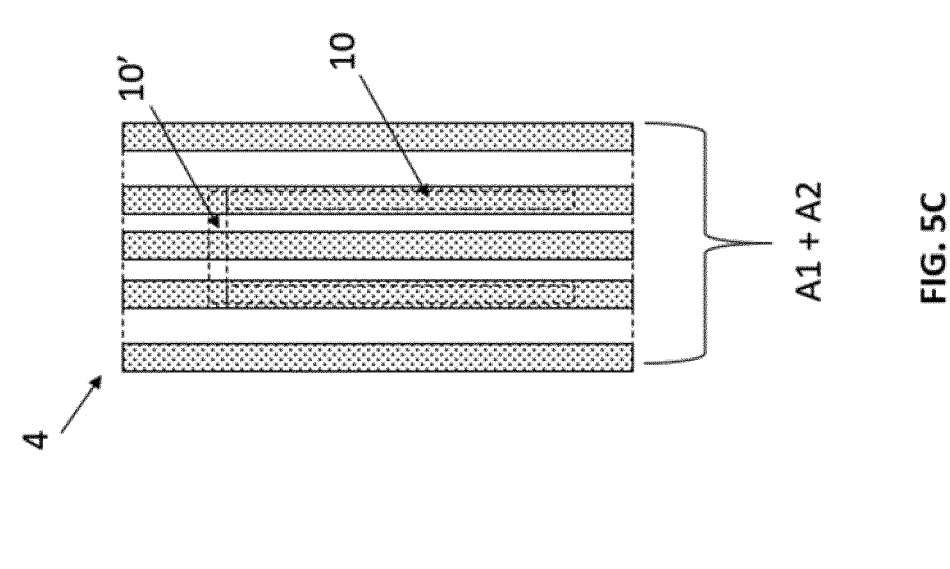
FIG. 5A-C schematically illustrate adhesive patterns according to embodiments of the present disclosure.
Figure 5B:
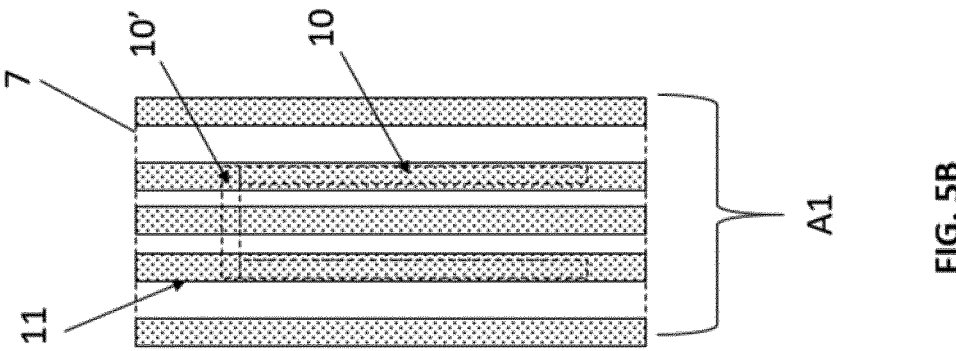
Figure 5A:
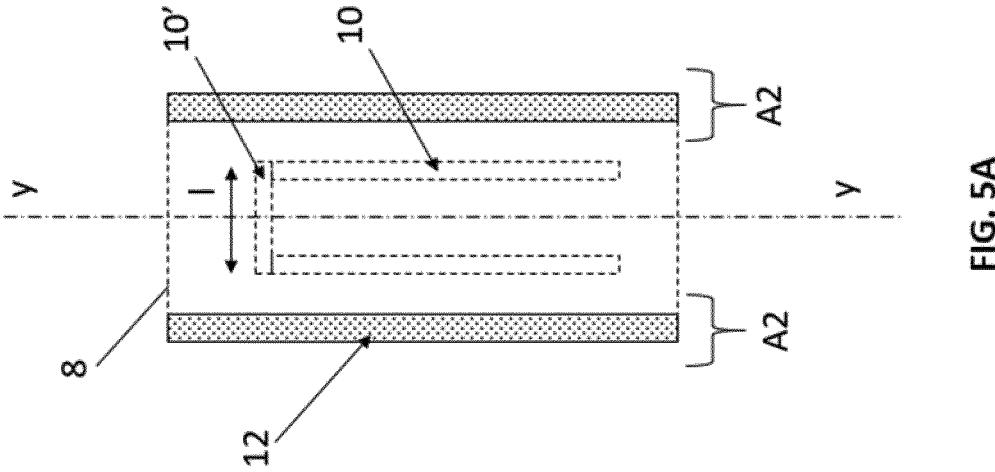

In an embodiment, the second adhesive area (A2) is free of stripe(s) crossing the transverse channel forming area (10'), this is exemplified in FIG. 5A-C. Advantageously, this arrangement allows for absence of some absorbent material sticking onto the corresponding transverse channel forming area of the bottom layer resulting in only two adhesion options, either adhered/glued or not adhered/glued. To the contrary, in embodiments where at least one stripe of the second adhesive area (A2) does cross the transverse channel forming area (10'), some absorbent material is stuck onto the corresponding transverse channel forming area of the bottom layer resulting in three adhesion options, either adhered/glued, partly adhered/glued, or not adhered/glued.

The Process of Making

Figure 6:
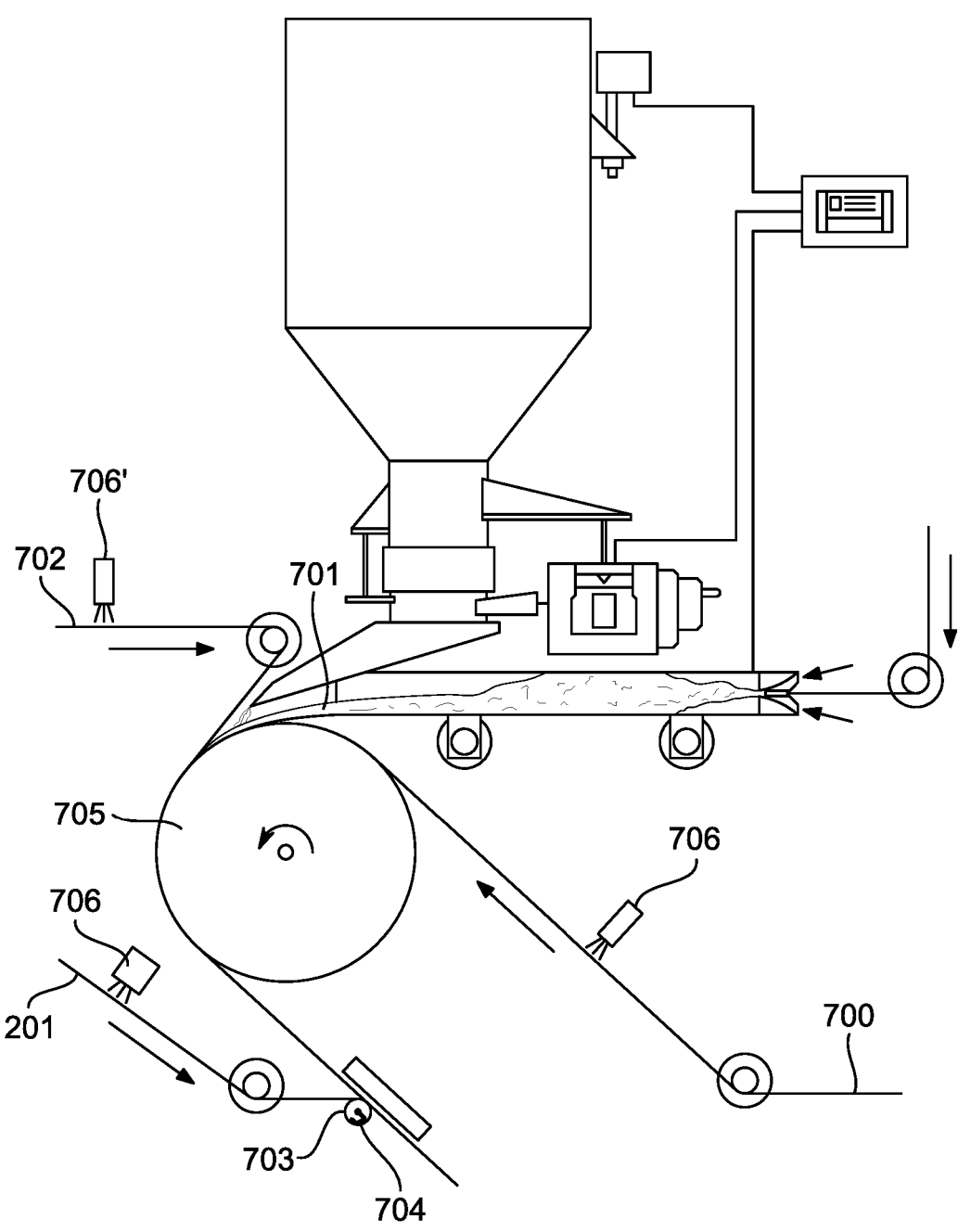
FIG. 6 schematically illustrates a method of making and apparatus for making articles, according to an embodiment of the present disclosure.
Figures 7A, 7B, 7C:
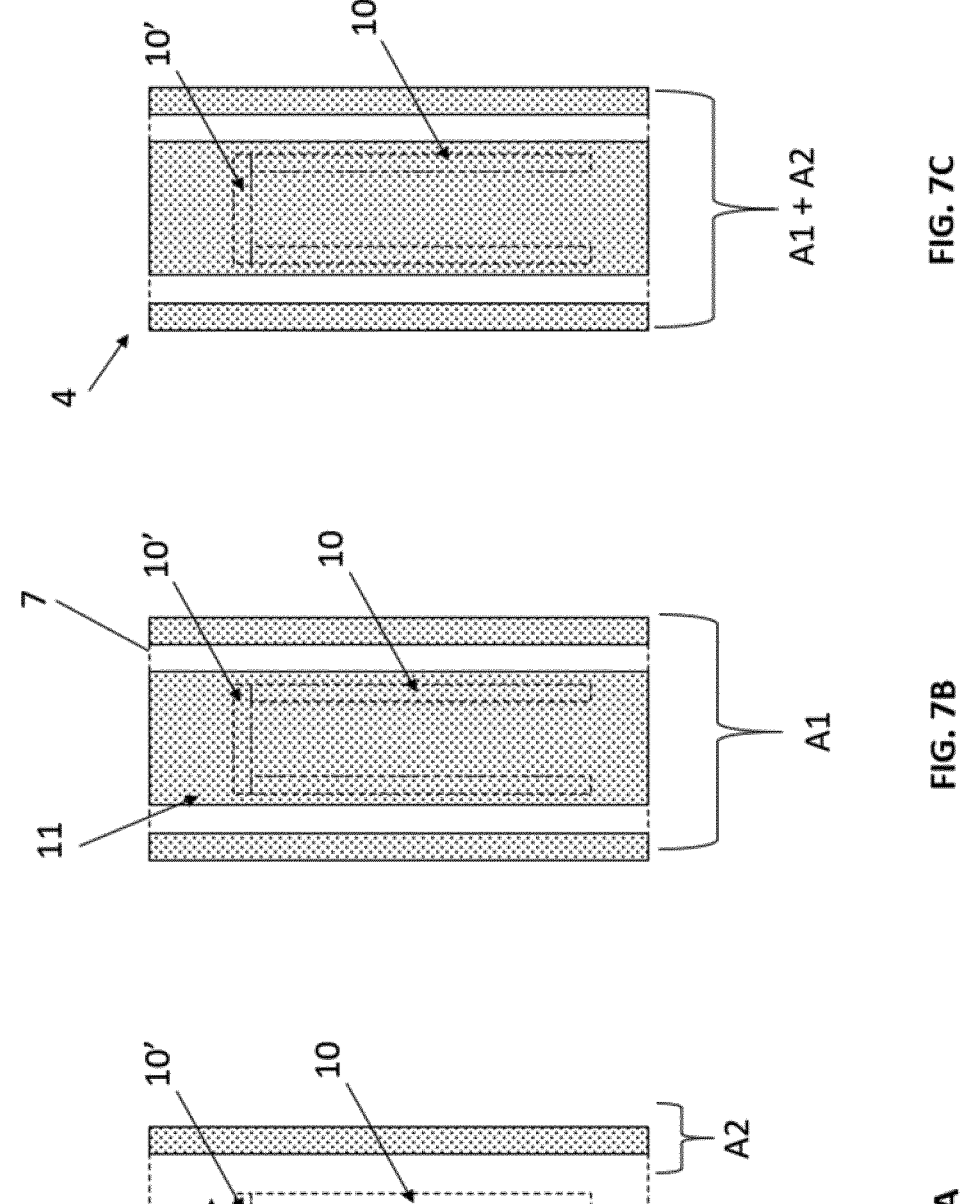
FIG. 7A-C schematically illustrate adhesive patterns according to embodiments of the present disclosure.

Referring to FIG. 6, the disclosure relates to a method for making an absorbent article comprising one or more channel forming areas, the method comprising the steps of:

i. providing a mold comprising a non-porous insert therein, wherein the mold is in fluid communication with an under-pressure source except for said insert;

ii. providing a first nonwoven web (700) this web generally forming the bottom core wrap (8) of the absorbent article core;

iii. applying a plurality of adhesive stripes to said first nonwoven web (700), said adhesive stripes comprising a second adhesive applied by a second adhesive applicator (706);

iv. depositing said first nonwoven web (700) to said mold such that said second adhesive faces away from said mold;

v. depositing an absorbent material, comprising cellulose fibers and/or superabsorbent polymer particles, over at least a portion of a surface of said nonwoven web (700) comprising said second adhesive;

vi. optionally removing said absorbent material from areas of the nonwoven web corresponding to said insert;

vii. applying one or more adhesive stripes to a second nonwoven web (702) this web generally forming the top core wrap layer (7) of the absorbent article core, said adhesive stripes comprising a first adhesive applied by a first adhesive applicator (706');

viii. depositing said second nonwoven web (702) directly or indirectly over the absorbent material, such to sandwich said absorbent material between top and bottom core wrap layers (7,8) formed by said first and second nonwoven webs (700,702);

ix. joining said top and bottom core wrap layers (7,8) together at least in the areas of the nonwoven webs corresponding to the insert to form an absorbent core having one or more channel forming areas (10) substantially free of absorbent material;

x. optionally joining an acquisition distribution system (201) to said absorbent core, typically a skin facing surface of said upper core wrap layer;

xi. optionally laminating said absorbent core and acquisition distribution system between a liquid pervious topsheet and a liquid impervious backsheet;

wherein said first adhesive forms a first adhesive area (A1) and said second adhesive forms a second adhesive area (A2), wherein said first adhesive area (A1) is greater than said second adhesive area (A2), and wherein at least one, preferably at least two, of the stripes of said first adhesive area (A1) overlap said channel forming areas (10). Advantageously, this process allows to attain an absorbent material having the advantages described in the previous section.

Preferably, the insert comprises at least two longitudinal members and at least one transverse member positioned between and connecting said at least two longitudinal members, such that the channel forming areas (10) are formed in step ix comprising at least two longitudinal channel forming areas extending along the longitudinal axis (y) and oppositely disposed such that said longitudinal axis (y) extends therebetween, and at least one transverse channel forming area (10') extending substantially perpendicular to said longitudinal axis (y), preferably wherein said transverse channel forming area (10') connects to said longitudinal channel forming areas at a position being selected from the group consisting of the front (F) of said article, the back (B) of said article, and combinations thereof.

Preferably, the transverse channel forming area (10') has a length (1) extending along an axis perpendicular to the longitudinal axis (y), and wherein at least one of the stripes of adhesive of the first adhesive area (A1) and/or second adhesive area (A2) crosses said transverse channel forming area (10'), such that the transverse channel forming area (10') comprises said first adhesive (11) over a length that is from 0.251 to 0.951, preferably from 0.31 to 0.91, even more preferably from 0.351 to 0.851, and/or wherein said transverse channel forming area (10') comprises said second adhesive (12) over a length that is less than 0.751, preferably less than 0.71, even more preferably from 01 to 0.651, even more preferably from 0.11 to 0.61, even more preferably from 0.151 to less than 0.51.

In an embodiment, step x. comprises the step of applying an adhesive pattern onto the acquisition distribution layer (typically the garment facing side thereof i.e. the side opposite the skin facing side thereof) or a skin facing surface of said upper layer of the core and laminating said acquisition distribution layer to said absorbent core wherein said adhesive pattern is positioned inboard and/or outboard of the channel(s) such that substantially no adhesive pattern overlaps with said channel(s), and typically wherein the acquisition distribution system comprises a spunbond and meltblown nonwoven layer or SM, SMS, SMMS and combinations thereof, layers. Alternatively, the acquisition distribution system comprises a carded thermobonded nonwoven. It has surprisingly been found that using such nonwoven layers and closely and/or directly adhering them to the core in such a way that no or little adhesive is present in the channel areas not only improves the rewet performance of the product by limiting sponge-like effects but further retains the high liquid draining performance of the channels.

Preferably, the pattern is in the form of a plurality of stripes or spirals being spaced apart in a transverse axis and extending along the longitudinal axis (y). Such patterns have been found most effective to ensure good coverage for tight adhesion of the layers whilst enabling the positioning thereof to substantially avoid overlap with the channels.

In an embodiment, step xi comprises the step of selectively applying pressure to the acquisition distribution layer and the absorbent core in the channel(s) such that said acquisition distribution layer is pressed into contact with the upper layer of the nonwoven web(s), preferably wherein said acquisition distribution layer is arranged to be in contact with said upper layer in dry state such to form one or more ditches and to freely displace away from said upper layer in wet state. Advantageously, this arrangement allows for fast transfer of the liquid to the channel in an initial stage and then as the absorbent material swells the acquisition distribution layer moves away from the channel promoting better dryness and allowing the absorbent material to absorb the collected liquid. The selective pressure may be carried out by a pressure roller (703) being profiled with one or more protrusions (704) for selectively applying pressure into the channels, nevertheless it would be apparent to a person skilled in the art that similar results may be achieved by other means such as pressure rollers coated with a pliable material, such as silicone, and adjusting the amount of pressure to be applied.

In an embodiment the acquisition distribution layer (201) may be first joined to a liquid permeable topsheet prior to then being joined to the upper layer of the core wrap of the absorbent core.

The mold cavities may be comprised in a plurality and arranged along a circumference of a rotating drum (705). The adhesive may be applied to the respective substrates via one or more adhesive applicators (706) that may be arranged to apply a spray and/or slot-coating of adhesive on respective substrates.

In an embodiment, the mold comprises a plurality of perforations or openings across its surface typically forming channels arranged to be in fluid (preferably air) communication with the under pressure source. Preferably, the insert (hereinafter also referred to as 3D insert) is positioned above and/or over said mold surface comprising a plurality of said perforations or openings and said 3D insert being free of said perforations or openings and consists of a solid component that is not in fluid communication with the under pressure source.

Preferably, the 3D insert has a cross-sectional shape selected from the group consisting of square, rectangular, oval, semi-circular, and combinations thereof.

More preferably, the 3D insert has the same or varying depth throughout the perimeter thereof.

In an embodiment, the 3D insert is 3D-printed, preferably made from a material selected from alumide, or is made from metal and formed by milling or casting.

In an embodiment, the adhesive is applied in zones across the width of the channels such to form zones, preferably alternating zones, of different bonding strength between the laminate. For example the first nonwoven web may be bonded to the second nonwoven web on at least three zones along the width of the channel. Such arrangement may comprise a first adhesive zone, a second adhesive zone and a third adhesive zone, the second adhesive zone being interposed between the first and third adhesive zones along the width of the channel (e.g. at an axis parallel to the core width and perpendicular to the longitudinal axis of the core) wherein the bonding strength of the second adhesive zone is greater than the bonding strength of the first and third adhesive zones. Examples of ways to achieve such stronger bonding strength in the second zone include using higher amounts of adhesive in this zone, applying greater mechanical pressure on this zone, or utilizing a different adhesive type, other ways are also contemplated provided a stronger adhesion between nonwoven webs results in such region. The different adhesive zones may comprise different adhesive stripes as described hereinabove.

In an embodiment the bonding strength in the first and third zones is less than the tensile force generated by the absorbent material located proximal to the channel upon wetting, such that the first and second nonwoven webs may separate in said zones upon wetting; and wherein the bonding strength in the second zone is greater than the tensile force generated by the absorbent material located proximal to the channel upon wetting, such that the first and second nonwoven webs may not separate in said zone upon swelling of the absorbent material and rather may remain fixedly joined. An advantage of this arrangement is that in dry conditions a noticeable channel is visible from the topsheet side of the article and/or core providing broad channels that are further useful for channeling more fluid particularly at initial/early discharge. This arrangement then further allows the bonding at the first and third regions to fail upon for example swelling of the SAP such to allow more volume to be available for expansion thereof (and prevent early saturation or non-optimal absorption), with typically the second zone resisting such expansion and thus providing integrity of the channels even in wet state.

In a preferred embodiment the first nonwoven web and/or the second nonwoven web, preferably the second nonwoven web, are elastic nonwovens (e.g. containing an elastic material such as Vistamaxx resin from ExxonMobil). An advantage of this embodiment is that the nonwoven web better and more easily wraps around the 3D insert upon application of a vacuum and permits subsequent joining to the first nonwoven web at a location corresponding to a position of the base of the 3D insert (opposite a protruding apex thereof). This has an advantage of limiting the formation of fluid collection basins or sinks within the channels.

More preferably, the channels are formed substantially only by said vacuum force and no additional mechanical action such as embossing.

In an embodiment, the adhesive is applied such that, when laminated, the adhered first and second nonwoven webs in the channel locations is substantially flush with the non-adhered portions of the second nonwoven web such to limit the formation of fluid retention pockets in the resulting laminated core. An advantage of this embodiment is to prevent the formation of pockets of fluid that may reduce comfort to the subject.

It is supposed that the present invention is not restricted to any form of realization described previously and that some modifications can be added to the presented example of fabrication without reappraisal of the appended claims.

The invention claimed is:

1. An absorbent article (1) comprising:
a liquid permeable topsheet (2),
a liquid impermeable backsheet (3), and
an absorbent core (4) positioned between said topsheet (2) and backsheet (3),
wherein the absorbent core (4) comprises an absorbent material (5), said absorbent material comprising cellulose fibers and/or superabsorbent polymers, and wherein said absorbent material is contained within at least one core wrap substrate (6) enclosing said absorbent material, and wherein a top layer (7) of said core wrap is adhered to a bottom layer (8) of said core wrap by a first adhesive (11) to form one or more channel forming areas (10) substantially free of said absorbent material, characterized in that said top layer (7) comprises said first adhesive (11) arranged to define a first adhesive area (A1) and said bottom layer (8) comprises a second adhesive (12) arranged to define a second area (A2), wherein said first adhesive area (A1) is greater than said second adhesive area (A2), and in that said first and second adhesive areas (A1, A2) comprise one or more adhesive stripes, wherein at least one of said adhesive stripes of the first adhesive area (A1) overlaps said channel forming areas (10), and wherein the second adhesive area (A2) comprises at least two spaced apart stripes of adhesive positioned outboard and/or inboard of the channel forming areas (10).

2. An absorbent article according to claim 1 wherein the second adhesive area (A2) consists of at least two spaced apart stripes of adhesive positioned outboard and/or inboard of the channel forming areas (10).

3. An absorbent article according to claim 1 wherein the first adhesive area (A1) consists of a plurality of spaced apart adhesive stripes wherein at least one of said adhesive stripes is positioned outboard and/or inboard of the channel forming areas (10).

4. An absorbent article according to claim 1 wherein the first adhesive area (A1) and second adhesive area (A2) form an area ratio A1/A2 that is greater than 1.5.

5. An absorbent article according to claim 1 wherein the at least one adhesive stripes of the first adhesive area (A1) that overlap said channel forming areas (10) comprise a first basis weight of said first adhesive, and wherein all other stripes of the first and second adhesive areas (A1, A2) comprise a second basis weight of first and/or second adhesive respectively, and wherein the first basis weight is from 150% to 800% greater than said second basis weight.

6. An absorbent article according to claim 5 wherein the first basis weight is from 2 g/m$^2$ to 8 g/m$^2$.

7. An absorbent article according to claim 1 wherein the first and second adhesive areas (A1,A2) substantially overlap each other such that they are not complementary.

8. An absorbent article according to claim 1 wherein the first adhesive area (A1) is arranged such that no adhesive is present between consecutive adhesive stripes, and wherein at least 2 of said stripes free of adhesive are comprised in the top layer (7) of the core wrap.

9. An absorbent article according to claim 1 wherein the second area (A2) is arranged such that no adhesive is present between consecutive adhesive stripes, and wherein at least 1 of said stripes free of adhesive are comprised in the bottom layer (8) of the core wrap.

10. An absorbent article according to claim 1 wherein the channel forming areas (10) comprise at least two longitudinal channel forming areas extending along said longitudinal axis (y) and oppositely disposed such that said longitudinal axis (y) extends therebetween, and at least one transverse channel forming area (10') extending substantially perpendicular to said longitudinal axis (y).

11. An absorbent article according to claim 10 wherein at least one of the stripes of the first adhesive area (A1) overlap at least a portion of the transverse channel forming area (10').

12. An absorbent article according to claim 10 wherein at least one of the stripes of the second adhesive area (A2) overlap at least a portion of the transverse channel forming area (10').

13. An absorbent article according to claim 1 wherein the adhesive stripes of the first and second adhesives (11,12) are arranged such that, when looked from a planar view, the absorbent core (4) comprises a plurality of stripes free of adhesive between said top layer (7) and bottom layer (8), wherein said plurality of stripes free of adhesive material are positioned inboard and/or outboard of the channel forming areas (10, 10').

14. An absorbent article according to claim 1 wherein the channel forming areas (10) comprise at least one transverse channel forming area (10') having a length (1) extending along an axis perpendicular to the longitudinal axis (y), and wherein at least one of the stripes of adhesive of the first adhesive area (A1) and/or second adhesive area (A2) crosses said transverse channel forming area (10'), such that the transverse channel forming area (10') comprises said first adhesive (11) over a length that is from 0.251 to 1.001 and/or wherein said transverse channel forming area (10') comprises said second adhesive (12) over a length that is less than 0.751.

15. A method for making an absorbent article comprising one or more channel forming areas, the method comprising the steps of:

i. providing a mold comprising a non-porous insert therein, wherein the mold is in fluid communication with an under-pressure source except for said insert;

ii. providing a first nonwoven web (700);

iii. applying a plurality of adhesive stripes to said first nonwoven web (700), said adhesive stripes comprising a second adhesive applied by a second adhesive applicator (706);

iv. depositing said first nonwoven web (700) to said mold such that said second adhesive faces away from said mold;

v. depositing an absorbent material, comprising cellulose fibers and/or superabsorbent polymer particles, over at least a portion of a surface of said nonwoven web (700) comprising said second adhesive;

vi. optionally removing said absorbent material from areas of the nonwoven web corresponding to said insert;

vii. applying one or more adhesive stripes to a second nonwoven web (702), said adhesive stripes comprising a first adhesive applied by a first adhesive applicator (706');

viii. depositing said second nonwoven web (702) directly or indirectly over the absorbent material, such to sandwich said absorbent material between top and bottom core wrap layers (7,8) formed by said first and second nonwoven webs (700,702);

ix. joining said top and bottom core wrap layers (7,8) together at least in the areas of the nonwoven webs corresponding to the insert to form an absorbent core having one or more channel forming areas (10) substantially free of absorbent material;

x. optionally joining an acquisition distribution system (201) to said absorbent core;

xi. optionally laminating said absorbent core and acquisition distribution system between a liquid pervious topsheet and a liquid impervious backsheet;

characterized in that said first adhesive forms a first adhesive area (A1) and said second adhesive forms a second adhesive area (A2), wherein said first adhesive area (A1) is greater than said second adhesive area (A2), and in that at least one of the stripes of said first adhesive area (A1) overlap said channel forming areas (10).

16. A method according to claim 15 wherein the insert comprises at least two longitudinal members and at least one transverse member positioned between and connecting said at least two longitudinal members, such that the channel forming areas (10) are formed in step ix comprising at least two longitudinal channel forming areas extending along the longitudinal axis (y) and oppositely disposed such that said longitudinal axis (y) extends therebetween, and at least one transverse channel forming area (10') extending substantially perpendicular to said longitudinal axis (y).

17. A method according to claim 16 wherein the transverse channel forming area (10') has a length (1) extending along an axis perpendicular to the longitudinal axis (y), and wherein at least one of the stripes of adhesive of the first adhesive area (A1) and/or second adhesive area (A2) crosses said transverse channel forming area (10'), such that the transverse channel forming area (10') comprises said first adhesive (11) over a length that is from 0.251 to 1.001 and/or wherein said transverse channel forming area (10') comprises said second adhesive (12) over a length that is less than 0.751.

18. An absorbent article according to claim 9 wherein at least 50% of the surface area of said bottom layer (8) is free of adhesive.

19. An absorbent article according to claim 10 wherein said transverse channel forming area (10') connects to said longitudinal channel forming areas at a position being selected from the group consisting of the front (F) of said article, the back (B) of said article, and combinations thereof.

20. An absorbent article according to claim 11 wherein none of the stripes of the second adhesive area (A2) overlap the transverse channel forming area (10').

\*   \*   \*   \*   \*